US005709705A

United States Patent [19]

Belcher

[11] Patent Number: 5,709,705

[45] Date of Patent: Jan. 20, 1998

[54] METHOD AND APPARATUS FOR REDUCING FACIAL WRINKLES

[76] Inventor: Pat E. Belcher, 120 Interstate N. Pkwy., East, Suite 424, Atlanta, Ga. 30339

[21] Appl. No.: 697,070

[22] Filed: Aug. 19, 1996

[51] Int. Cl.$^{6}$ .......... A61B 17/00

[52] U.S. Cl. .......... 606/204.35; 601/120

[58] Field of Search .......... 606/204.35; 601/115–135

[56] References Cited

U.S. PATENT DOCUMENTS

| | | | |
|---|---|---|---|
| 472,572 | 4/1892 | Forest . | |
| 2,011,471 | 8/1935 | Casagrande et al. . | |
| 2,079,096 | 5/1937 | Wilson . | |
| 2,621,652 | 10/1952 | Ehrhardt . | |
| 2,633,844 | 4/1953 | Herndon . | |
| 2,691,978 | 10/1954 | Kirby . | |
| 4,345,757 | 8/1982 | Lo Voi | 601/121 |
| 4,433,683 | 2/1984 | McCoy et al. | 601/120 |
| 4,554,911 | 11/1985 | Nielsen . | |
| 4,566,442 | 1/1986 | Mabuchi et al. . | |
| 4,883,047 | 11/1989 | Guitay . | |
| 4,989,585 | 2/1991 | Auker . | |
| 5,218,955 | 6/1993 | Gueret . | |
| 5,458,561 | 10/1995 | Schweisfurth . | |

FOREIGN PATENT DOCUMENTS

| | | | |
|---|---|---|---|
| 644707 | 10/1928 | France | 601/120 |

*Primary Examiner*—Michael Buiz
*Assistant Examiner*—William W. Lewis
*Attorney, Agent, or Firm*—Kennedy, Davis & Kennedy, P.C.

[57] ABSTRACT

Facial wrinkles are reduced by rolling the face and scalp with implements having free wheeling rollers.

10 Claims, 1 Drawing Sheet

METHOD AND APPARATUS FOR REDUCING FACIAL WRINKLES

TECHNICAL FIELD

This invention relates to methods and apparatuses for use in reducing facial wrinkles.

BACKGROUND OF THE INVENTION

Facial wrinkles are a fact of life for many people who simply accept them although most would prefer that they not exist. The aging process itself is the normal cause although wrinkles can also be caused by dramatic changes in weight, from smoking, from the sun, and even from chronic stress and fatigue.

Heretofore efforts at reducing facial wrinkles have included the self use of skin creams and facial masks. Professional procedures have principally included the use of chemical peels and the injection of collagen to replace the loss of natural collagen. A purified form of the bacteria that causes botulism has also been injected on the theory that the bacteria weakens the response of the nerve endings in the facial skin and relaxes the surrounding muscles that cause the wrinkles.

The use of creams and masks is messy and unsightly and has proved to have only limited effectiveness. Chemical peels and collagen injections are costly, often painful, and have in instances posed serious health hazards. Indeed, the injection of collagen is believed by many rheumatologists and epidemiologists to cause autoimmune diseases in some cases.

Accordingly, it is seen that a need has long existed for a simple, safe and inexpensive method and apparatus for use in reducing facial wrinkles. It is to the provision of such that the present invention is primarily directed.

SUMMARY OF THE INVENTION

It has now been discovered that facial wrinkles may be reduced by a procedure wherein the face is rolled with a roller until the face is flushed and warmed. Both the face and the scalp are then rolled with increased pressure. After this facial wrinkles, such as those located about the eyes and lips, are rolled with firm pressure for a period of time in excess of the combined periods of time taken rolling the face to flushness and in rolling the face and scalp.

A kit for use in reducing facial wrinkles comprises first, second and third implements. The first implement has a rod, a handle fixedly mounted to the rod, and rollers having cylindrical skin contact surfaces also mounted to the rod for free rotating thereon. The second implement has a rod, handles fixedly mounted to opposite ends of the rod, and rollers with cylindrical skin contact surfaces mounted to the rod for free rotation thereon between the handles. The third implement has a rod, a handle fixedly mounted to one end of the rod, and a roller with a convex peripheral skin contact surface mounted to the rod for free rotation thereon. The kit may be used in practicing the method of the invention.

BRIEF DESCRIPTION OF THE DRAWING

The drawing is a perspective view of three implements show in FIGS. 1A, 1B and 1C that provide an apparatus that incorporates principles of the invention in its preferred form and which may be used in practicing the inventive method of the invention.

DETAILED DESCRIPTION

The Apparatus

Figure 1A:
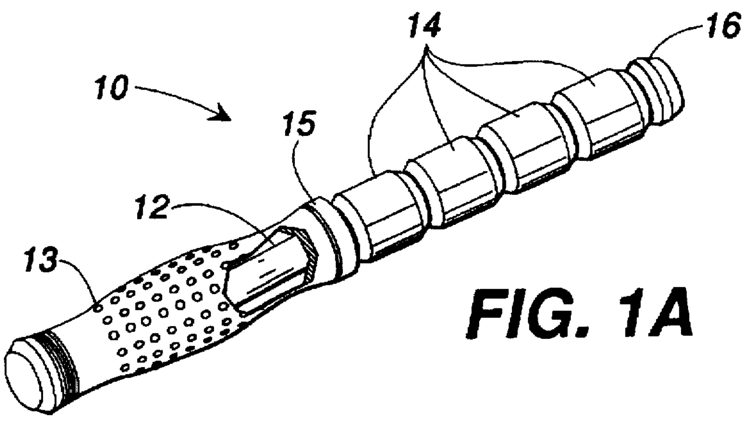

Referring now in more detail to the drawing, there is shown in FIG. 1A a first implement 10 having a solid acetal rod to one end of which is rigidly mounted a hand grip 13 made of heavy vinyl to provide a handle. Four nylon rollers 14 with cylindrical peripheral surfaces are mounted to the rod 12 for free rotation thereon. These rollers are all of the same size and shape and are spaced from the hand grip 13 by a rotatable PVC spacer 15. The set of rollers is maintained in axial position on the rod by a stainless steel push nut 16 rigidly mounted to the end of the rod 12 distally from the hand grip.

Figure 1B:
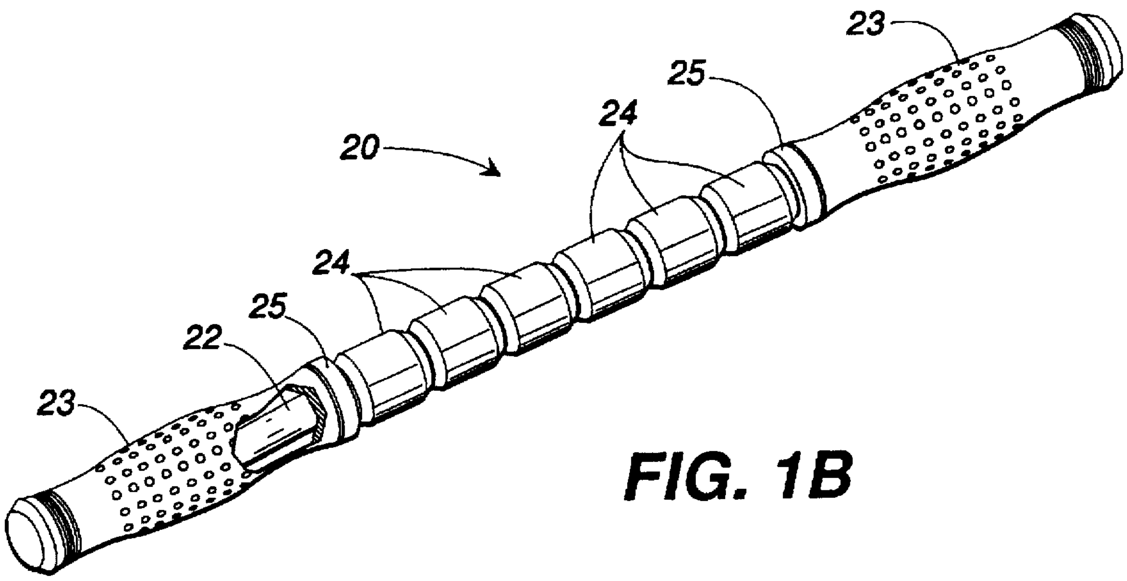

The second implement 20 of the apparatus is shown in FIG. 1B to comprise a solid acetal rod 22 to opposite ends of which two hand grips 23 are rigidly mounted. Six nylon rollers 24 with cylindrical peripheral surfaces are mounted to the rod 22 for free rotation thereon. These rollers are all of the same size and shape as those of the implement 10 and are spaced from the two hand grips by two PVC spacers 25.

Figure 1C:
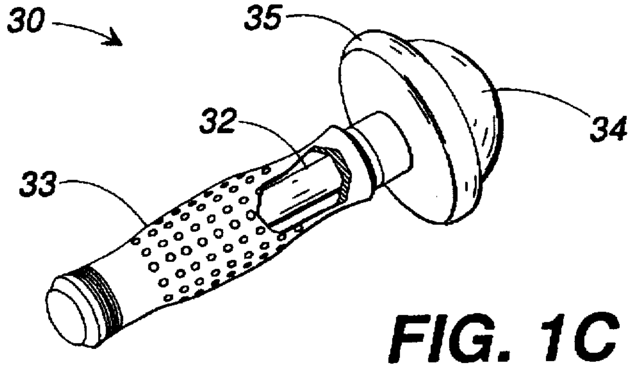

The third implement 30 of the apparatus is shown in FIG. 1C to comprise an acetal or galvanized steel rod 32 to which is rigidly mounted a hand grip 33 of the same size, shape and configuration as those of implements 10 and 20. A nylon wheel 34 is mounted to an end of the rod 32 for free rotation thereon. The wheel 34 has a substantially semi-circular, convex, annular peripheral skin engaging surface 35. The wheel 34, being 1¾ inches in diameter, is larger than the rollers of the two implements 10 and 20.

Method of Operation

The just described apparatus is used as a myofascial release tool that is usually self-applied to the face and head to remove or reduce facial wrinkles in a non-invasive manner. As previously stated, skin aging and consequent wrinkles are linked to collagen and to ground substance degradation. Atrophic changes of the skin can be linked to reduced blood supply that deprives the tissue of nutrients and oxygen. Localized contracted bands of muscle and fascia have similar effects underneath the wrinkled skin. Remediation involves a profusion of nutrient dense and oxygen laden blood to the deprived tissues. This can be done with the myofascial release implements 10, 20 and 30 to provide progressively deeper release to skin, fascia and muscle lesions. Implement 10 is used to stimulate skin perfusion by performing rapid back and forth superficial passes over the entire face with attention directed to the deep forehead wrinkles and crows feet around the eyes. The passes are made both up and down and sideways. Rapid back and forth movements with implement 10 cause increased blood flow to the facial skin with resulted skin warming.

Next, implement 20 is used to penetrate deeper into the fascia and muscles over both the face and head. In this manner myofascial release procedures are applied to major muscles of the head including the occipitalis, frontages, and temporals which often contain trigger points that alter facial turgor. This implement is held with both hands and applied generally perpendicularly to the wrinkles. Rolling of the scalp encourages perfusion to the occipitalis muscle and surrounding fascia. Both temporal regions are rolled by holding the implement 20 generally vertically and applying a more pressure in rolling it back and forth over the temporals muscle including the crows feet and surrounding fascia. This implement is used slower than implement 10 with skin wrinkles rolled omnidirectionally much as a laundress would do in ironing a shirt. In doing this trigger points are identified which are painful contracted bounds of muscle. Once identified the implement is applied with emphasis placed on muscles that contain trigger points. It has been found that three minutes twice a day with implement 20 yields good results although it may be applied for longer periods.

The implement 30 is next used to target the deeper tissue located beneath non-compliant skin and fascia. It is applied deeply into muscle tissue with special attention placed on inactivating muscle trigger points. It is held with either hand and applied with back and forth movements with gentle pressure. It is applied around the eye sockets, crows feet, upper cheeks, jowls and around the mouth and nose with focus placed on the masseter muscle. Three minutes, twice a day, has been found to yield good results.

Practice of the above described practice begins to yield reliable results in approximately 14 days. However, more lengthy or frequent treatment can hasten the onset of visible remediation. Although implement 30 has been found by many to be the most productive of the three implements, the use of all three is preferred as then the companion layers of new complaint skin, fascia and muscle are all treated. In doing so implement 30 should be used for a period of time equal to or greater than the combined periods of time that implements 10 and 20 are also used during any single treatment session. If implement 10 is not first used, then implement 30 should be used for a longer period of time than implement 20. Thus, if any implement or step is to be omitted, that should be the first step using implement 10.

It is thus seen that a method and kit is now provided for alleviating or reducing facial wrinkles. While the treatment protocol and kit have been described in their preferred forms, it should be understood that many variations and modifications may be made thereto without departure from the spirit and scope of the invention as set forth in the following claims.

I claim:

1. A method of reducing facial wrinkles comprising the steps of (a) rolling the face with a roller until the face is flushed and warmed, (b) rolling substantially the entire head with a roller with pressure applied to the head greater than the pressure applied to the face in step (a), and (c) rolling facial wrinkles about the eyes or lips with a roller with firm pressure applied to the wrinkles for a period of time in excess of the combined periods of time consumed in performing steps (a) and (b).

2. The method of claim 1 wherein step (a) the face is rolled for between approximately two and three minutes.

3. The method of claim 1 wherein step (b) the head is rolled for between approximately two and three minutes.

4. The method of claim 2 wherein step (b) the head is rolled for between approximately two and three minutes.

5. The method of claim 1 wherein step (c) facial wrinkles are rolled for between approximately 30 and 45 minutes.

6. A kit for use in reducing facial wrinkles comprising first, second and third implements for use in sequence and with said first implement having a rod, handles fixedly mounted to one portion of said rod, and a plurality of rollers having cylindrical skin contact surfaces mounted to another portion of said rod for free rotation thereon; and with said second implement having a rod, a handle fixedly mounted to opposite end portions of said rod, and a plurality of rollers having cylindrical skin contact surfaces mounted to said rod for free rotation thereon between said handles; and with said third implement having a rod, a handle fixedly mounted to one end of said rod and a roller having a convex peripheral skin contact surface mounted to the other end of said rod for free rotation thereon.

7. The kit of claim 6 wherein said third implement roller has a diameter greater than the diameter of said first implement roller and greater than the diameter of said second implement rollers.

8. The kit of claim 6 wherein said third implement roller has a convex peripheral skin contact surface of an axial width less than the axial width of the combined skin contact surfaces of said first implement plurality of rollers and less than the axial width of the combined skin contact surfaces of said second implement plurality of rollers.

9. The kit of claim 6 wherein said rods of said first, second and third implements are acetal.

10. The kit of claim 6 wherein said rollers of said first, second and third implements are nylon.

* * * * *